United States Patent [19]

Pass

[11] Patent Number: 5,818,056
[45] Date of Patent: Oct. 6, 1998

[54] OPTICALLY STIMULATED LUMINESCENCE DOSIMETRY IN DENTAL ENAMEL

[75] Inventor: Barry Pass, Halifax, Canada

[73] Assignee: Dalhousie University, Halifax, Canada

[21] Appl. No.: 835,699

[22] Filed: Apr. 10, 1997

[51] Int. Cl.$^6$ .................................................. G01N 21/63
[52] U.S. Cl. .................. 250/458.1; 250/337; 250/459.1; 356/318
[58] Field of Search ........................... 250/458.1, 459.1, 250/461.1, 337; 356/317, 318

[56] References Cited

U.S. PATENT DOCUMENTS

| | | | |
|---|---|---|---|
| 4,290,433 | 9/1981 | Alfano | 356/318 |
| 4,894,547 | 1/1990 | Leffell et al. | 250/461.1 |
| 5,028,794 | 7/1991 | Miller . | |
| 5,194,916 | 3/1993 | Hayashi | 356/318 |
| 5,272,348 | 12/1993 | Miller . | |
| 5,581,356 | 12/1996 | Vezard | 250/461.1 |

OTHER PUBLICATIONS

Flourescence in dissolved fractions of human enamel, Ulrika Hafstrom–Bjorkman, Folke Sundstrom, and Jap. ten Bosch, 1990.

Application of Optically Stimulated Luminescence to the Dosimetry of Recent Radiation Events Involving Low Total Absorbed Doses; D.I. Godfrey–Smith and E.H. Haskell, 1993.

A New Method of Retrospective Biophysical Dosimetry: Optically Stimulated Luminescence and Fluorescence in Dental Enamel, D. I. Godrey–Smith, B. Pass, R. Scallion, Jul. 27, 1995.

Primary Examiner—Edward J. Glick
Assistant Examiner—Darren M. Jiron
Attorney, Agent, or Firm—Jon Carl Gealow

[57] ABSTRACT

A method and apparatus for determining radiation absorbed dose using optically stimulated luminescence (OSL) in dental enamel. The invention is based on the determination that OSL can be induced in dental enamel and can be used for determining absorbed radiation dose, for example during unmonitored x-rays, or accidental exposures to ionizing radiation. In particular, it has been discovered that there is a dose dependent OSL in dental enamel. The present invention makes possible a non-invasive, sensitive, reliable and portable method and apparatus for in vivo human radiation dosimetry.

19 Claims, 3 Drawing Sheets

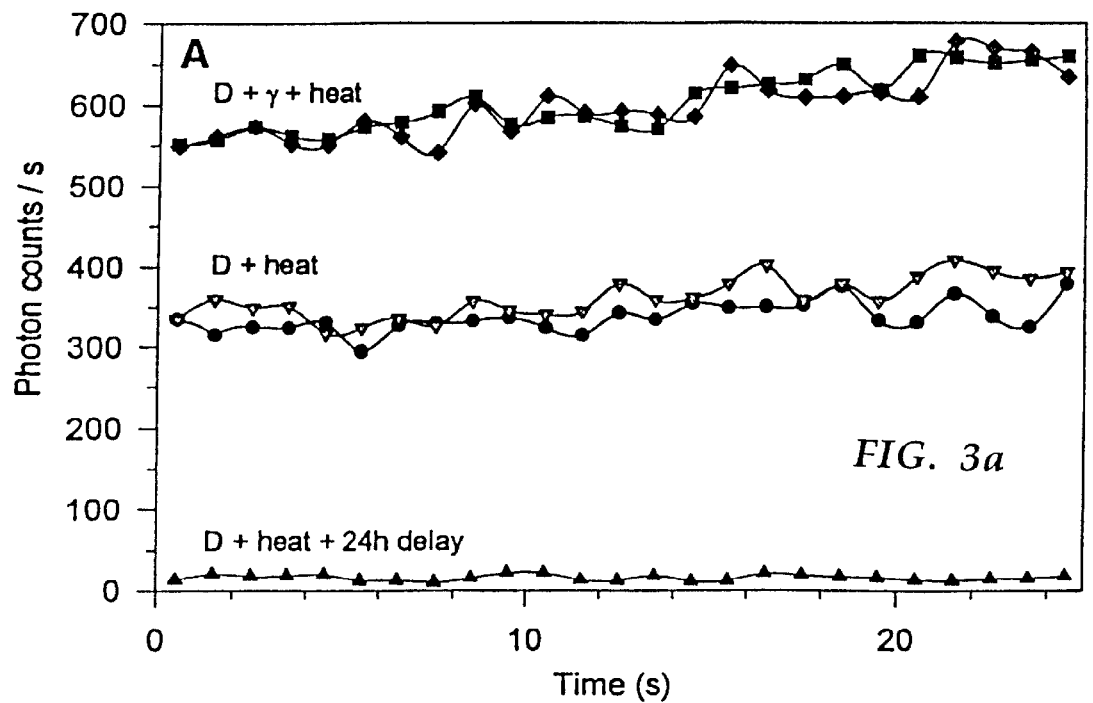
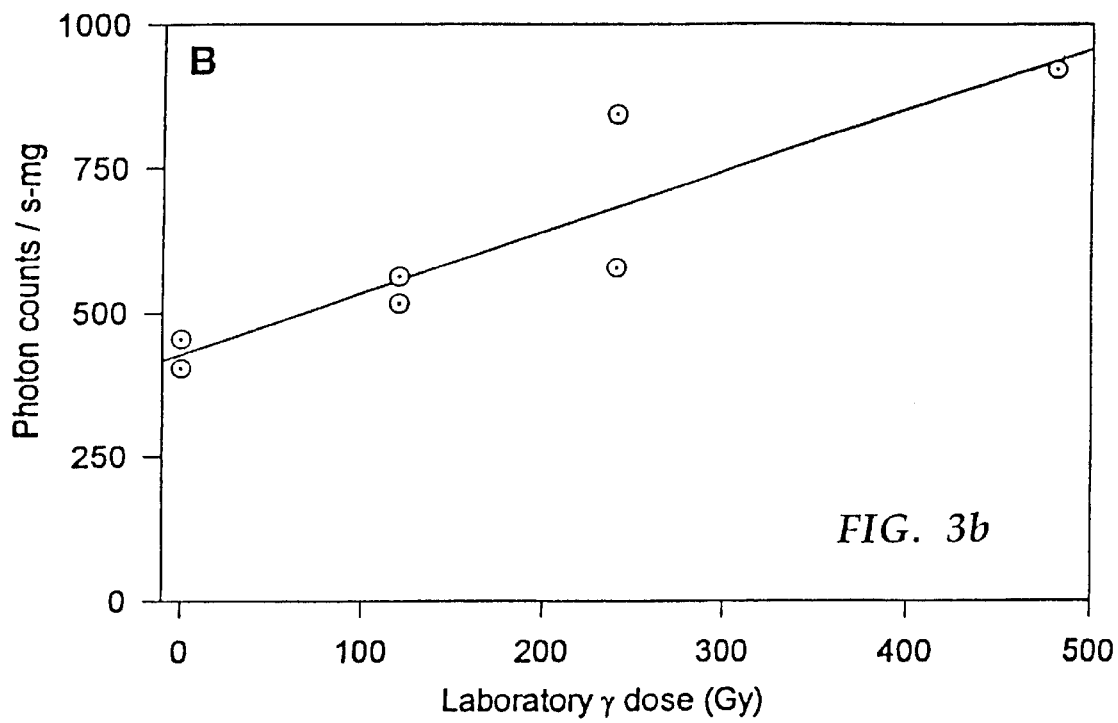

OPTICALLY STIMULATED LUMINESCENCE DOSIMETRY IN DENTAL ENAMEL

BACKGROUND OF THE INVENTION

Determination of the radiation exposure history of the general population has become increasingly important in the study of the effects of low level radiation. Of necessity the effects of low radiation levels are conventionally deduced by extrapolation of the effects at medium radiation levels, data at low levels being difficult to obtain. Alternatively, acute radiation accident dosimetry presently provides the best means of estimating radiation risk by extrapolating its effects to lower doses. In addition, it can provide a means of triage for determining therapeutic strategies and prognosis. Finally, radiation accident dosimetry can be of forensic value in postmortem investigations and it can aid in understanding the accident process itself.

A major goal of radiation dosimetry is to establish causality in areas such as the prediction of health effects, risk assessment, and radiation protection. A major obstacle to this goal is the difficulty in establishing dose-response relationships for individuals or populations.

Biological techniques involve the study of chromosome aberrations in blood lymphocytes and the kinetics of granulocyte and lymphocyte production following the exposure. There are difficulties in reconstructing a valid biologically relevant dose and in assessing appropriate outcomes. Most biological indicators are not a measure of accumulated dose but an indication of the biologically significant dose. Further, biological, dosimetry is not without its limitations. It is transient, technically difficult, and of limited sensitivity.

When ionizing radiation interacts with matter it deposits some of its energy in the mineral lattice of crystalline insulators. The energy is stored in the form of charges trapped at metastable defects in the gap between the valence and conduction bands. The understanding of the storage and release of radiation energy trapped in the lattices of natural minerals has led to the development of three related dosimetric analytical and dating techniques. These techniques are electron spin resonance, thermoluminescence and optically stimulated luminescence.

Electron spin resonance (ESR) is used to detect free electrons produced by radiation and is a measure of absorbed dose. ESR is commonly applied to dating and to radiation dosimetry of natural hydroxyapatite in dental enamel and clothing of the victim. ESR in dental enamel is a good surrogate of absorbed dose. However, it provides no information about biological impact, is not a direct measure of whole body dose and is subject to confounding factors such as the effect of ingested beta-emitters. There is also a problem of inter-sample (different teeth from the same or different individuals) variability in sensitivity to radiation. Further, ESR is limited in sensitivity (10 cGy) and requires a large array of laboratory equipment and extracted teeth if dental enamel is to be used.

Thermoluminescence (TL) is used to measure the radiation doses absorbed by quartz, feldspar and artificial minerals for purposes of dating. For example, radiation workers conventionally wear badges containing lithium fluoride. After exposure to radiation, the badges are heated and the amount of emitted light is measured. While TL has been proposed for determining absorbed dose in dental enamel and bone, its use is limited as the application of heat burns the organic content of the sample. Thus it is not a technique suitable for in vivo dosimetry or in vitro dosimetry for samples having organic content.

There is a requirement for a dosimetric technique which can detect the amount of radiation absorbed in humans in vivo, and without the requirement of complex laboratory equipment. Such a device would permit monitoring of radiation exposure in the general population. Consequently, large random population samples can be monitored to directly relate radiation exposure and its sequelae (e.g. cancer). This can lead to direct, as opposed to extrapolated, determinations of radiation risk.

SUMMARY OF THE INVENTION

Optically stimulated luminescence (OSL) is a method which determines the level of absorbed radiation dose in natural or artificial mineral substances. In OSL, the mineral is stimulated with low energy visible or infrared photons. Absorption of visible photons leads to ejection of the charges into the conduction band. Subsequently, luminescence is emitted as a result of recombination of the de-trapped charges with holes in the bandgap. The number of photons emitted by the substance are proportional to the radiation dose absorbed at some earlier time. Thus, OSL is very well suited to retrospective dosimetry in situations where the dose absorbed is unknown. OSL was developed as a means of dating geological sediments, quartz, feldspar and artificial minerals and in particular, is applied to the detection of low radiation doses in quartz.

It has been discovered that OSL can be induced in dental enamel and can be used for determining absorbed radiation doses in humans and other dentate animals, for example during unmonitored x-rays, or accidental exposures to ionizing radiation. In particular, it has been discovered that there is a radiation dose dependent OSL in dental enamel. The present invention is based on the discovery that visible photon stimulation of dental enamel produces a radiation dose dependent luminescence due to recombination, as it does in quartz, feldspar and other known minerals. Thus the present invention makes possible a non-invasive, sensitive, reliable and portable method and apparatus for human radiation dosimetry.

In accordance with the present invention, there is provided a method for determining radiation dose absorbed by a dentate animal comprising exposing dental enamel of said animal to a source of incident optical photons effective to stimulate luminescence in said enamel, detecting the intensity of said luminescence, and determining absorbed radiation dose on the basis of said detected intensity.

In accordance with another aspect of the present invention, the step of determining radiation dose comprises correlating the detected intensity of said luminescence to intensities produced by samples of dental enamel that have absorbed known doses of radiation.

In accordance with another aspect of the present invention, there is provided a device for determining absorbed radiation dose in a dentate animal comprising a source for exposing dental enamel with optical photons effective to stimulate luminescence therein, a detector effective to detect the intensity of said luminescence and means for determining absorbed radiation dose on the basis of said detected intensity.

In accordance with another aspect of the present invention, the means for determining comprises data storage means for storing data representative luminescence intensities produced by samples of dental enamel that have absorbed known doses of radiation and comparator means for correlating the detected intensity to said stored data.

In accordance with another aspect of the present invention, the incident optical photons are infrared photons and the luminescence is detected in the broadband visible range.

In accordance with another aspect of the present invention, the incident optical photons are green visible photons and the luminescence is detected in the ultraviolet range.

The method and apparatus of the present invention can be used in vivo or in vitro. When used in vitro, the dental enamel can be natural or deproteinated and can be heated prior to exposure with photons.

BRIEF DESCRIPTION OF THE DRAWINGS

FIG. 3a is a graphical representation showing the broadband visible luminescence signal of deproteinated dental enamel stimulated with infrared photons as a function of time for radiated and unirradiated samples showing the effect of the application of heat.

FIG. 3b is a graphical representation showing the broadband visible luminescence signal of deproteinated dental enamel stimulated with infrared photons as a function of dose.

DESCRIPTION OF THE PREFERRED EMBODIMENTS

The following experimental procedure was performed to determine the dose dependency of OSL in human tooth enamel.

The samples used were fragments of modern tooth enamel. Dentin was separated from the enamel by slowly removing it with a dental hand drill. The clean enamel was then slowly crushed in a mortar and pestle and sieved to obtain grains less than 355 $\mu$m in size. Half of the crushed sample was deproteinated using a treatment adapted from that described by Kolberg and Prydz, Calcif. Tiss. Res. 17:9–23; 1974. Approximately 95 mg of enamel chips were placed in a paper envelope made from Whatman #2 filter paper, and placed inside another made from Whatman #1 filter paper. This was placed in a small beaker to which 35 ml of 2N NaOH was added. The beaker was placed in a water bath at 80° C. for 1 h. After treatment the sample was rinsed twice with distilled water and air dried.

Aliquots were prepared by depositing approximately 7.5 mg of crushed enamel on cleaned, HF-etched Al disks of 10 mm diameter, 0.8 mm thickness, which had first been lightly coated with Dow Corning 200 silicon oil, and briefly preheated on a bench-top hot plate. Radiation doses were administered using a calibrated $^{60}$Co g source (AECL Gamma Cell 220), with a known dose rate of 2 Gy/min.

The OSL was measured in a 24-position automated TL/OSL-DA-12-A reader manufactured by the Risø National Laboratory, Roskilde, Denmark, Infrared (IR) stimulation was performed using an array of 32 GaAs diodes, with emission centered at 880±80 nm and 40 mW incident power on the sample. Green stimulation was performed using a 75 W quartz envelope tungsten filament lamp (Osram HLX64616), restricted with long pass glass (Schott GG420) and gel (Lee 010 Medium Yellow, $T_{\lambda \leq 460\ nm} < 0.2$) filters, and an IR-suppressing short pass interference filter (Lys & Optik). This filtering provided a stimulating spectrum of 523±37 nm at full width half mean (FWHM), with negligible emission for $\lambda \leq 460$ nm.

The detection system was based on a 5 cm Thorn-EMI 9236QA bialkali photomultiplier (peak quantum efficiency at 375 nm). Depending on the stimulation mode, luminescence was detected either in the UV or the broadband visible range. IR-stimulated luminescence was detected in the broadest visible range possible, restricted only by a Schott BG39 pale blue glass filter to suppress detection of the stimulating IR photons. Green-stimulated luminescence was detected through a UV-transmitting Hoya U340 glass filter ($T_{max}$ at 340 nm, FWHM=75 nm). This sharp restriction was necessary to prevent any of the visible stimulating photons from being detected.

Figure 1:
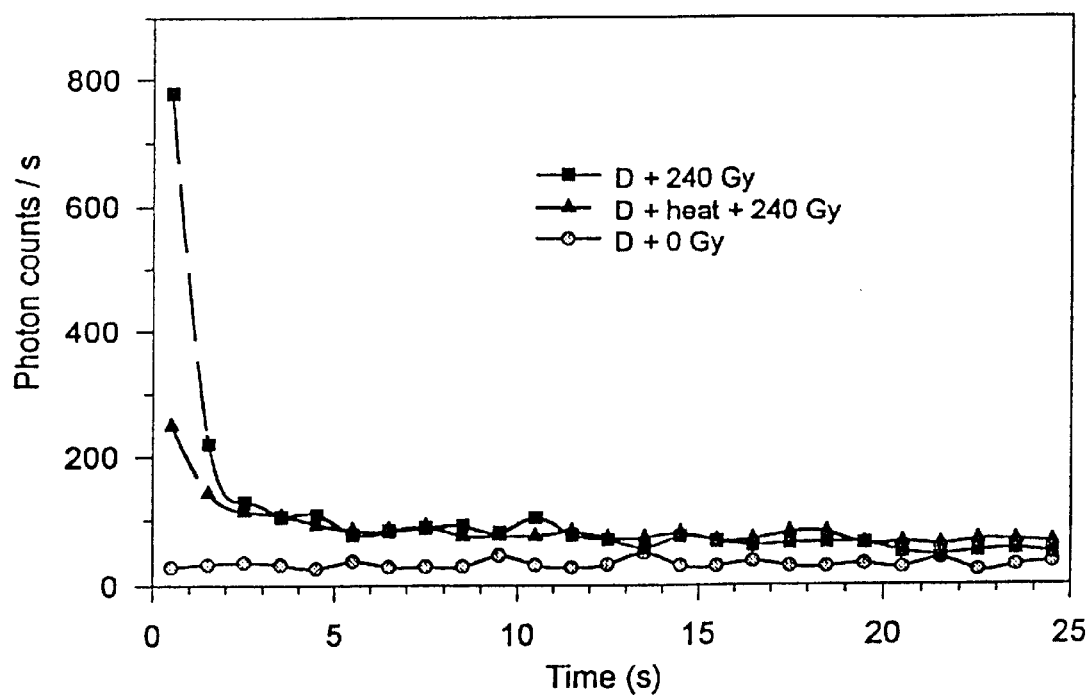
FIG. 1 is a graphical representation showing the UV luminescence signal of deproteinated dental enamel stimulated with green photons as a function of time for different radiation doses.

The UV luminescence signals for three deproteinated aliquots stimulated with green photons are shown in FIG. 1. The deproteinated aliquot which had been irradiated with 240 Gy (D+240 Gy) yielded a transient, time dependent UV luminescence signal. The control aliquot which had received no radiation (D+0 Gy) and an aliquot that was heated to 450° C. following γ radiation (D+240 Gy+heat) yielded no net luminescence (responses being identical to instrumental background), confirming that the luminescence from the irradiated aliquot was due to radiation. Subsequent irradiation after the 450° C. heating (D+heat+240 Gy) again yielded a time dependent green stimulated luminescence. However, the absolute intensity of the post heating dose response luminescence is about three times lower than the dose response luminescence emitted without prior heating. This sensitivity change indicates that caution must be used in attempts to apply the regeneration method described by Godfrey-Smith and Haskell, Health Physics 65 (396–404) 1993 with any preheating treatments to retrospective dosimetry of enamel using green photon stimulation.

Figure 2A:
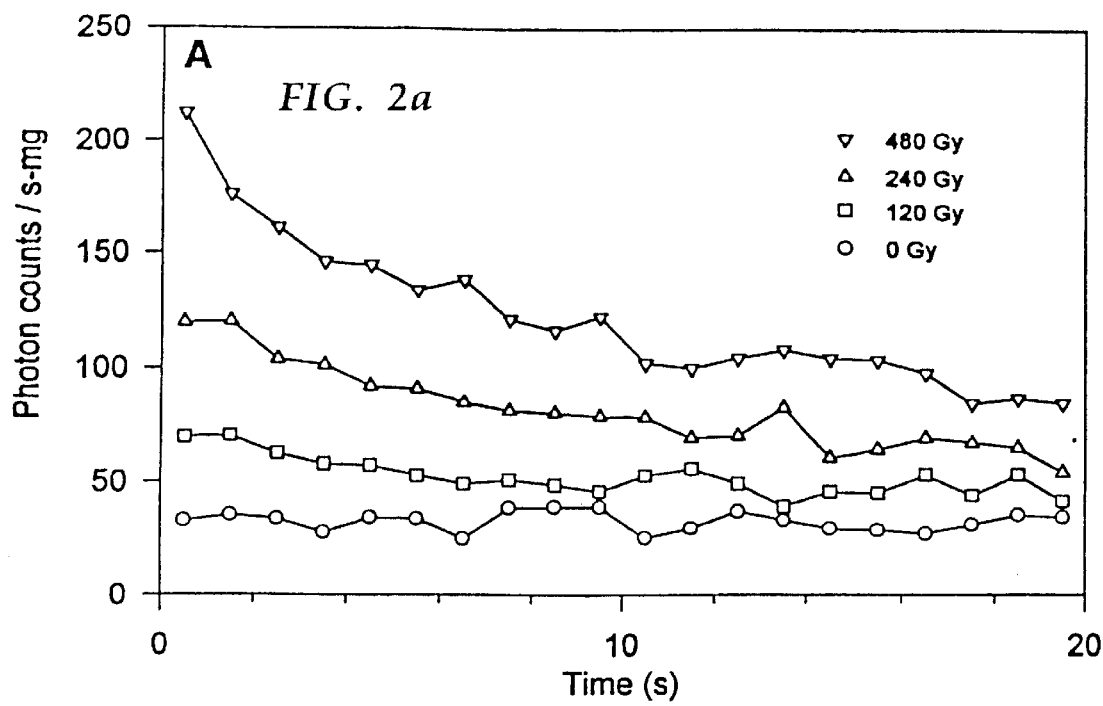
FIG. 2a is a graphical representation showing the broadband visible luminescence signal of deproteinated dental enamel stimulated with infrared photons as a function of time for irradiated and unirradiated samples.
Figure 2B:
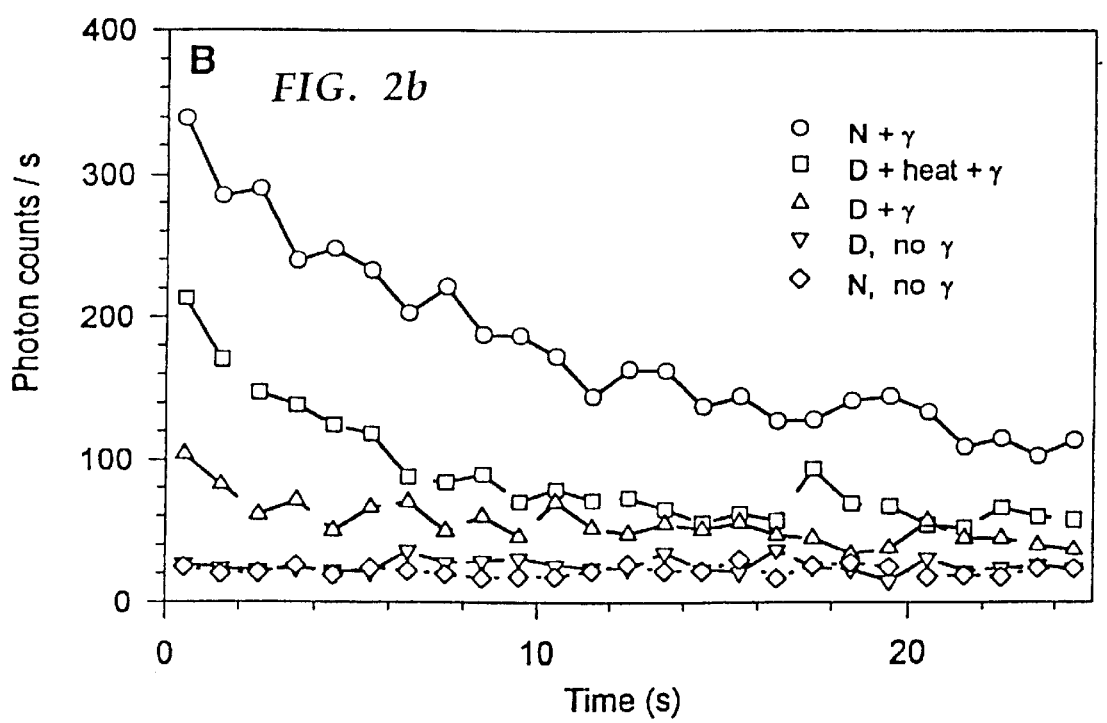
FIG. 2b is a graphical representation showing the broadband visible luminescence signal of natural and deproteinated dental enamel stimulated with infrared photons as a function of time for radiated and unirradiated samples.

Broadband visible luminescence for four deproteinated aliquots stimulated with infrared photons and irradiated with 0, 120, 240 and 480 Gy is shown in FIG. 2a. The aliquots yielded a time dependent luminescence proportional to absorbed gamma radiation dose. The decrease over time of luminescence resulting from stimulation of irradiated aliquots is a dear indication of optical eviction of charges from traps. The decay in the case of infrared stimulation luminescence is much slower than the decay of the green stimulated luminescence, as can be seen by comparing the respective 240 Gy responses. This implies that the photoefficiency in inducing recombination depends on the energy of stimulating photons.

Broadband visible luminescence for aliquots stimulated with infrared photons and irradiated with 0 or 120 Gy is shown in FIG. 2a. The 0 Gy dose responses for undeproteinated (N, no γ), deproteinated (D, no γ) aliquots yielded no luminescence and are identical to instrument background. The 120 Gy dose responses for undeproteinated (N+γ), deproteinated (D+γ) and deproteinated and heating to 450° C. prior to irradiation (D+heat+γ) aliquots are also shown. The results indicate that deproteinated aliquots heated to 450° C. prior to subsequent irradiation have a greater dose-dependant infrared stimulated luminescence sensitivity than do unheated deproteinated aliquots. Further, the irradiated undeproteinated aliquots have a greater dose dependent infrared stimulated luminescence sensitivity than do deproteinated aliquots. It is believed that heating and irradiation causes interactions between the fluorescence centres and luminescence in the mineral and organic components of hydroxyapatite.

The effect of heating to 450° C. irradiated and non-irradiated deproteinated aliquots which had their dose dependent infrared stimulated luminescence erased by prolonged (1–2 min) photon stimulation is shown in FIG. 3a. Measured immediately prior to heating, the net broadband visible luminescence responses of the aliquots were zero. Immediately after heating to 450° C., a nearly time independent infrared stimulated luminescence was observed for the (D+heat) aliquots. The signal for two sets of two different but identically prepared aliquots are shown in FIG. 3A. This signal was observed continuously to 45 second, it was not detectable after a post-heating delay of 24 hours (D+heat+24 h delay). A time independent but significantly higher response was observed for the aliquots that received a radiation dose of 120 Gy prior to heating (D+heat+γ) as compared to the aliquots that received no radiation. To demonstrate this effect, a dose response curve for deproteinated aliquots using radiation doses of 0, 120, 240 and 480 Gy after heating to 450° C. is shown in FIG. 3b. Luminescence output is integrated over the first 10 seconds, for doses of 0–480 Gy. The results suggest that irradiation plus heating creates new centres which act to enhance the IR sensitivity of the enamel. Repetition of this experiment with green photons yielded no luminescence, indicating that the effect is restricted to the visible emission band of hydroxyapatite. It is believed that prompt post-heating IR stimulated response is related at least in part, to fluorescence of residual organic content in the enamel.

In accordance with the present invention, it has been discovered that OSL in dental enamel is a bio-physical surrogate of absorbed radiation dose. A radiation dependent and time dependent OSL has been demonstrated in dental enamel. Since the OSL signals are proportional to absorbed radiation doses, OSL can be used for radiation dosimetry of hydroxyapatite from tooth enamel. The existence of a time dependent OSL in deproteinated enamel and undeproteinated enamel permit the technique to be used for retrospective dosimetry on extracted teeth and in vivo. Further, heat treatment prior to and post-irradiation affects IRSL. This can have application for in vitro retrospective radiation dosimetry where extracted teeth are used.

In order to correlate the intensity of luminescence response with absorbed radiation dose, dose-response curves or relational data can be experimentally established over the range of absorbed dose to be monitored, which for most practical applications will be from about 1 cGy to about 100 Gy. The curves or data will be established for the particular photon source and detection apparatus to be used. Such curves or data can be established for natural and deproteinated tooth enamel that have been exposed to known radiation doses. The measured luminescence response can then be correlated to absorbed dose with the use of the dose-response curves or data.

It will be recognized by those skilled in the art that the particular photon source and the particular luminescence detection apparatus used will not necessarily be the same as that described above. In particular, the stimulating photon source can advantageously be a laser of sufficient power and possessing a well-defined selectable visible frequency spectrum providing a choice of photon frequencies between infrared and ultraviolet. The luminescence detector can be a photocell, solid state photomultiplier or detector. Not only can such devices lower the detection limit to typical lifetime doses from background radiation (eg. 10 cGy), as is required for a device to survey radiation exposure in the general population, the stimulation and detection optics are easily miniaturized and thus can be incorporated in a portable or hand held non-invasive instrument that can be used for in vivo testing. The device can employ fibre optics to transmit the stimulating radiation and collect the luminescence. Ancillary electronics will accomplish the detection and counting of photons, calibration of the luminescence signal and generation of a radiation dose readout. The device can include a means for controlling the optical source to provide a predetermined exposure of optical photons and a means for controlling the detector to detect the intensity of said luminescence over a predetermined interval after exposure. Data representing the dose-response curve using correlative exposure and detection parameters can be stored in electronic format in a memory device associated with the instrument and can be used to directly correlate the measured response to absorbed radiation dose. In the alternative, an appropriate calibration algorithm can be established and stored to convert the detected luminescence response to radiation dose.

We claim:

1. A method for determining absorbed radiation dose in a dentate animal comprising:
    exposing dental enamel of said animal to a source of incident optical photons effective to stimulate luminescence in said enamel;
    detecting the intensity of said luminescence;
    determining absorbed radiation dose on the basis of said detected intensity.

2. The method of claim 1 wherein said step of determining comprises correlating the detected intensity of said luminescence to intensifies produced by samples of dental enamel that have absorbed known doses of radiation.

3. The method of claim 2 wherein said dental enamel is stimulated with a predetermined exposure of photons and said detection is performed over a predetermined interval after exposure.

4. The method of claim 1 wherein the incident optical photons are infrared photons and the luminescence is detected in the broadband visible range.

5. The method of claim 1 wherein the incident optical photons are green visible photons and the luminescence is detected in the ultraviolet range.

6. The method of claim 1 wherein said incident optical photons are derived from a laser source.

7. The method of claim 1 wherein the dental enamel is exposed and said luminescence is detected in vivo.

8. The method of claim 1 wherein the dental enamel is exposed and said luminescence is detected in vitro.

9. The method of claim 8 wherein the dental enamel is deproteinated prior to exposure.

10. The method of claim 8 wherein the dental enamel is heated prior to exposure.

11. A device for determining absorbed radiation dose in a dentate animal comprising a source for exposing dental enamel with optical photons effective to stimulate luminescence therein, a detector effective to detect the intensity of said luminescence and means for determining absorbed radiation dose on the basis of said detected intensity.

12. The device of claim 11 wherein said means for determining comprises data storage means for storing data representative of luminescence intensities produced by samples of dental enamel that have absorbed known doses of radiation and comparator means for correlating the detected intensity to said stored data.

13. The device of claim 12 further including means for controlling said source to provide a predetermined exposure of optical photons and means for controlling said detector to detect the intensity of said luminescence over a predetermined interval after exposure.

14. The device of claim 11 wherein the source is a variable photon source capable of selectively producing frequencies between infrared and ultraviolet.

15. The device of claim 11 wherein the source is an infrared photon source and the detector is capable of detecting luminescence in the broadband visible range.

16. The device of claim 11 wherein the source is green visible photon source and the detector is capable of detecting luminescence in the ultraviolet range.

17. The device of claim 11 wherein the source is a laser.

18. The device of claim 11 wherein the source and detector are mounted in a unitary instrument adapted to be manually positionable into close proximity to said dental enamel.

19. The device of claim 18 wherein the unitary instrument is hand held and portable.

* * * * *